United States Patent
Yang et al.

[11] Patent Number: 5,902,273
[45] Date of Patent: May 11, 1999

[54] PRESSURIZABLE EPIDURAL SPACE IDENTIFICATION SYRINGE

[76] Inventors: Ian Y. Yang; James Z. Yang, both of 3288 Reservoir Oval E, Apt. 702, Bronx, N.Y. 10467

[21] Appl. No.: 09/133,634

[22] Filed: Aug. 13, 1998

Related U.S. Application Data

[60] Provisional application No. 60/062,132, Oct. 15, 1997.

[51] Int. Cl.[6] .................................................... A61M 5/00
[52] U.S. Cl. ............................................ 604/118; 600/561
[58] Field of Search .................................. 604/121, 118; 128/DIG. 13; 600/561

[56] References Cited

U.S. PATENT DOCUMENTS

| | | |
|---|---|---|
| 2,024,967 | 12/1935 | Dierker .................................... 604/121 |
| 2,646,042 | 7/1953 | Hv ........................................... 604/118 |
| 3,920,002 | 11/1975 | Dye et al. ............................... 604/118 |
| 4,162,673 | 7/1979 | Patel . |
| 4,175,567 | 11/1979 | Patel . |
| 4,215,699 | 8/1980 | Patel . |
| 4,231,715 | 11/1980 | Gleichner ................................ 604/121 |
| 4,284,084 | 8/1981 | Binard et al. . |
| 4,623,335 | 11/1986 | Jackson . |
| 4,642,095 | 2/1987 | Harle ....................................... 604/118 |
| 4,795,440 | 1/1989 | Young et al. ........................... 604/118 |
| 4,801,293 | 1/1989 | Jackson . |
| 4,944,724 | 7/1990 | Goldberg et al. . |
| 5,024,662 | 6/1991 | Menes et al. . |
| 5,163,904 | 11/1992 | Lampropoules et al. ............... 604/121 |
| 5,188,594 | 2/1993 | Zilberstein . |
| 5,205,828 | 4/1993 | Kedem . |
| 5,270,685 | 12/1993 | Hagen et al. ........................... 604/121 |
| 5,336,186 | 8/1994 | Greelis et al. .......................... 604/121 |
| 5,470,316 | 11/1995 | Tovey et al. ............................ 604/118 |
| 5,470,317 | 11/1995 | Cananzey et al. ..................... 604/121 |
| 5,517,846 | 5/1996 | Caggiani . |
| 5,531,696 | 7/1996 | Menes . |
| 5,643,213 | 7/1997 | McPhee . |
| 5,707,356 | 1/1998 | Paul ........................................ 606/118 |
| 5,722,955 | 3/1998 | Racz ....................................... 604/121 |

*Primary Examiner*—Paul J. Hirsch
*Attorney, Agent, or Firm*—Arjun S. Sanga

[57] ABSTRACT

A syringe that can be positively pressurized via a one-way valve and illustrated by a pressure indicator is designed to be used with an epidural needle to identify epidural space and to protect the dura being punctured when a loss of positive pressure occurs. The inventive syringe housing having a plunger with a longitudinal bore for pressurization is connected to a pressure chamber via the one-way valve allowing air flow only into the pressurization chamber from the syringe housing. A needle is air-tightly connected to the pressurization chamber with a needle connecting device. A pressure indicator connected to the pressurization chamber objectively indicates the loss of positive pressure when the needle enters the epidural space. The positively pressurized air from the needle deflects the dura away from the needle tip and prevents dural puncture. Methods for detecting the epidural space and deflecting the dura using this inventive syringe are also provided.

11 Claims, 3 Drawing Sheets

PRESSURIZABLE EPIDURAL SPACE IDENTIFICATION SYRINGE

RELATED APPLICATIONS

This application is based on U.S. Provisional Application Ser. No. 60/062,132, filed Oct. 15, 1997.

TECHNICAL FIELD

The present invention relates to a positively pressurizable syringe for detecting the epidural space and protecting the dura matter in the spinal column of mammals, particularly humans. In particular, the present invention relates to a spinal epidural syringe capable of indicating and maintaining positive pressurization therein. The inventive epidural syringe includes a pressurization chamber which communicates through a needle to deflect the dura matter and permits safe insertion of that needle into the epidural space for detection thereof.

BACKGROUND

To avoid the side-effects of drugs on the brain, analgesic or anesthetic drugs can be delivered to the spinal cord by placing the drugs outside of the membranous sac containing the spinal cord. Between this sac, called the dura, and the overlying spinal ligaments, is a potential space called the spinal epidural space (SES). It is a potential space because normally the anatomy here is juxtaposed until the space is crested. Placing drugs in the SES blocks spinal cord functions including pain transmission permitting either pain control (analgesia) or complete loss of all sensation (anesthesia) for surgery.

In clinical practice, locating the SES with a needle is technically difficult. The greatest danger for the novice is to sense the change in resistance as the needle passes through the spinal ligaments before the needle inadvertently passes through the SES and penetrates the dura. In other words, one seeks to reach the SES and stop before going through the dura.

Epidural anesthesia or analgesia is one of the most popular regional anesthetic procedures employed for surgery, obstetrics, postoperative analgesia, and chronic back pain management. The potential risk involved in this procedure is the accidental puncture of the dura. Identification of the precise moment when the needle is advanced into the epidural space decreases the likelihood of that risk.

Present methods for identifying this space fall into two categories: the "loss of resistance" and the "hanging drop" techniques. The former is the most commonly adopted technique to identify the space due to the lack of precision in the latter.

The loss of resistance technique involves direction of the epidural needle through the skin into the interspinous ligament. Then, the stylet of the needle is removed and an air-tight and free sliding glass syringe, containing air, or saline is connected to the needle. If the needle tip is properly positioned within the substance of the interspinous ligament, injection will not be possible; this is defined as the feeling of resistance. At this point, most textbooks suggest for the noninjecting hand to advance the needle with the thumb and index finger grasping the hub of the needle while the dorsum of the hand rests on the patient's back for stabilization. The injecting hand is placed on the plunger of the syringe with gentle but continuous pressure. As the needle passes through the ligarnentum flavum and enters the epidural space, a sudden loss of resistance occurs. The medication can then be injected with precision into the epidural space.

There are several disadvantages to this technique. First, the method described above is especially difficult for a novice because experience is required to obtain coordination of the two hands which are functioning differently. Next, because of the lack of an objective visual indicator, this method is difficult to supervise and results in a high incidence of dural puncture among novices.

The "loss of resistance" technique has widely been alternated involving a two-handed grip on the syringe and needle with continuous firm pressure on the hub. As the needle is advanced a few millimeters, one will stop and check the location of the needle by gently depressing the plunger and confirming whether the needle tip is still within the ligament or has moved to the area where loss of resistance occurs. The apparent disadvantage of this method is that in between stops, the needle could have advanced through the epidural space and punctured the dura.

The "hanging drop" technique capitalizes upon the loss of pressure experienced when the needle enters the epidural space. A drop of saline solution is placed on the open hub of the needle. The drop "hangs" on the needle until the needle enters the epidural space, when the needle tip indents the dura resulting in negative pressure and the drop is "sucked" into the needle from the change in pressure. This indicates that the needle should be stopped as it has entered the epidural space.

Regardless of the technique used, locating the epidural space can be a difficult endeavor for both novices and experts because it is a potential space between two tissues held together by a slight negative pressure. Dural puncture is the greatest risk when there is error and sequelae of this mistake can range from spinal headaches to lethal total spinal anesthesia.

SUMMARY OF THE INVENTION

The preferred embodiment of the present invention has a pressurizable chamber containing a one-way valve for positive pressure build-up and an attached pressure indicator to identify the loss of positive pressure when the needle enters the epidural space. Thus, the invention utilizes the "loss of positive pressure" technique. Assembled to the pressure chamber are a syringe housing attached to the valve side of the pressure chamber, and a needle connector with locking device on the opposite side for air-tight connection with an epidural needle. There is a longitudinal bore or channel in the center of the plunger as an air passage. When the plunger is pulled outwardly, air will be drawn in from the longitudinal bore due to the negative pressure build-up in the syringe housing. When the plunger is pushed inwardly with the thumb covering the exposed open end of the longitudinal bore on the plunger, air will be pushed into the pressure chamber through the one-way valve.

The pressure indicator consists generally of a housing defining an indicator section and a pressurizable section, which is divided into two separate portions by a septum. The proximal portion is the continuation of the pressure chamber in air flow communication with the syringe. It consists of a bellows, a counterbalance spring, and an indicator. The open end of the bellows is air-tightly sealed against the septum of the case effectively facilitating the environment outside the bellows pressurizable. Within the bellows the spring spans the length of the bellows with one end attached to the septum and the other attached to the bottom of the bellows; thus the spring effectively counterbalances the bellows once compressed. The indicator stands vertically within the spring and extends into the distal portion of the case, its end attached to the bottom of the bellows. As positive pressure builds up in the chamber, the bellows will be compressed against the elastic force of the spring indicated by the elevation of the indicator.

When the epidural needle reaches the epidural space, the positively pressurized air will deflect the dura matter away from the needle tip as it escapes from the chamber, through the needle, and into the epidural space. The positive pressure in the chamber will drop immediately, and the indicator will return to its original position due to the elastic force of the spring. This will objectively signify the identification of the epidural space.

An object of this invention is to provide an operator with a constantly pressurized syringe for identification of the epidural space for epidural anesthesia or analgesia.

Another object of this invention is to provide an epidural syringe which has enough positive pressure to effectively deflect the dura matter upon entrance of the needle into the epidural space, thus effectively preventing dural puncture.

Another object of this invention is to provide an epidural syringe which can be re-pressurized when pressure is lost in soft tissue rather than in the epidural space when the needle enters the surrounding loose connective tissue, the repressurization for determining the needle location.

Another object of this invention is to provide an operator with a pair of relatively free and more coordinated hands for steady needle advancing.

Another object of this invention is to provide both the operator and the observers with an objective and visual indication of "loss of positive pressure" for ease of use and training.

An additional object is to lower the manufacturing cost of the syringe by employing low cost plastic materials, replacing expensive, specially made, air-tight, and free sliding glass syringe.

DETAILED DESCRIPTION OF THE PREFERRED EMBODIMENTS

Figure 1:
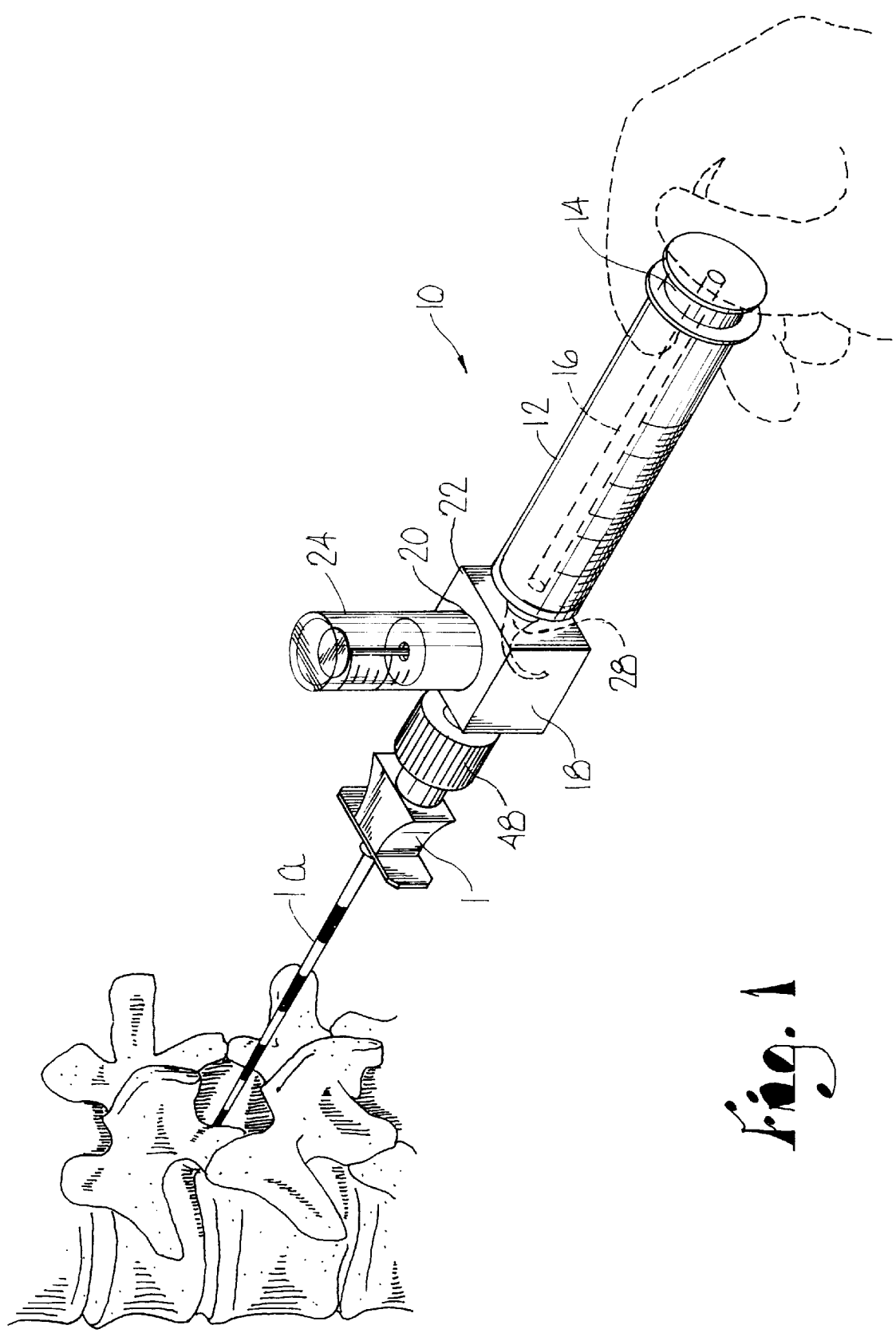
FIG. 1 is a side perspective view of the invention in its operable position illustrating the needle inserted into the interspinous ligament.

In describing the preferred embodiment of the invention, which is illustrated in the drawings, specific terminology will be resorted to for the sake of clarity. However, it is not intended that the invention be limited to the specific terms so selected and it is to be understood that each specific term includes all technical equivalents which operate in a similar manner to accomplish a similar purpose.

Figure 2:
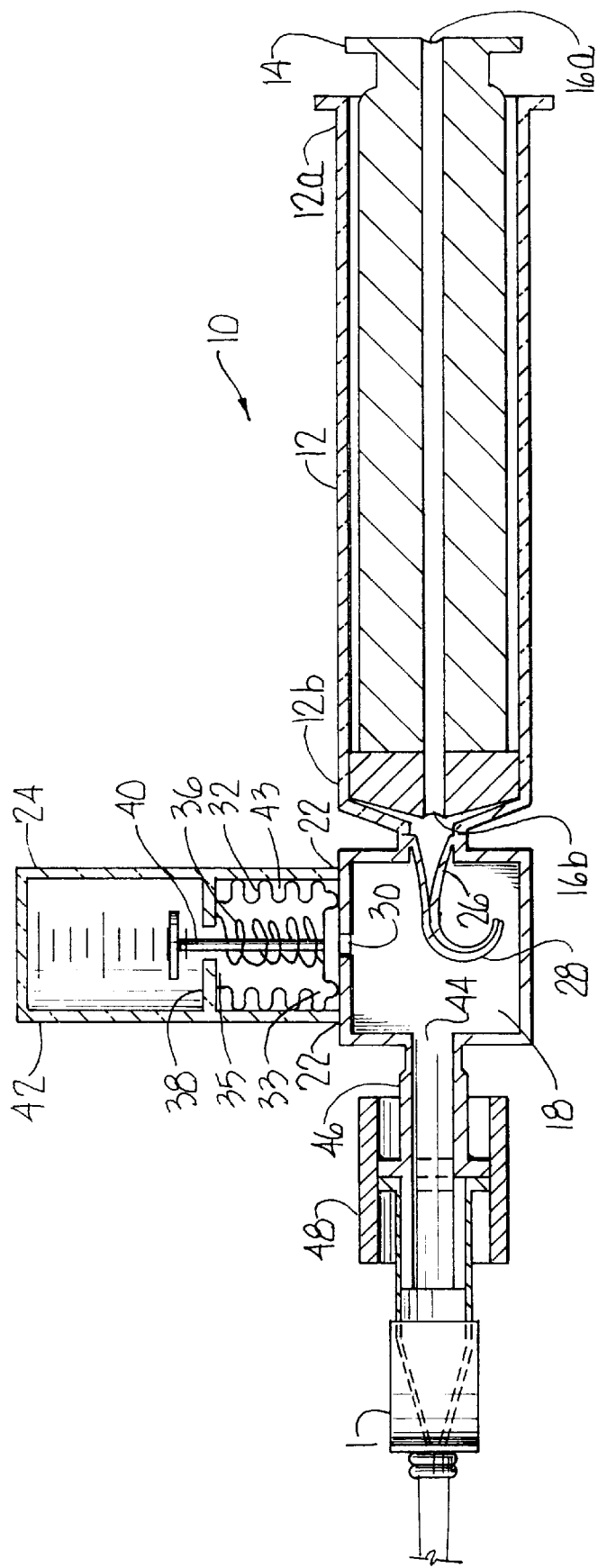
FIG. 2 is a cross-sectional view of the invention with the plunger in its original position and the pressure indicator at zero level.

Referring to FIGS. 1 and 2, an improved syringe 10 has a syringe housing 12 open at first and second ends 12a, 12b and slidably fitted with a plunger 14 at the first end 12a of syringe housing 12. Syringe 10 is preferably molded plastic although glass, ceramic or any other suitable material may be employed in one or more pieces. A longitudinal bore 16, open at an exposed end 16a and open at an enclosed end 16b extends inside the length of the plunger 14 allowing air passage from outside the syringe 10 through longitudinal bore 16 and into the syringe housing 12.

As shown in FIG. 2, a pressure chamber 18 is attached to the syringe housing 12. Pressure chamber 18 consists generally of a housing 20 defining a pressurization section 22 and an indicator section 24 in the preferred embodiment. Pressurization section 22, while cube-shaped in the preferred embodiment, may be of any suitable shape. Indicator section 24 is made of a transparent plastic material and visible within the chamber. Pressurization section 22 of pressure chamber 18 contains a first aperture 26 for air flow communication between pressurization section 22 and the second end 12b of syringe housing 12. The first aperture 26 of pressurization section 22 contains a one-way valve 28. One-way valve 28 only opens to allow air passage from syringe housing 12 into pressurization section 22. One-way valve 28 is made of silicon rubber material and forms a tubular membrane. It is molded and juxtaposed with one end air-tightly fitted within the first aperture 26. The free end of the valve is slightly folded retrogradely to maintain a closed position.

As shown in FIG. 2, pressurization section 22 contains a second aperture 30 for air communication with indicator section 24. Within indicator section 24, bellows 32 define a seat 34 sitting against second aperture 30. Bellows 32 and seat 34 are made of silicon rubber material and molded into one piece. Spring 36 is made of a metal material and placed within bellows 32. Spring 36 and closed end 33 of bellows 32 seat against seating flange 38 for seating biasing spring 36 and bellows 32 against seating flange 38. Open end 35 of bellows 32 is air-tightly secured against seating flange 38. Indicator bar 40 is placed within spring 36 and extends past seating flange 38 into the distal region 42 of indicator section 24. In the preferred embodiment indicator bar 40 is a T-shaped bar pointer, although any appropriate bar may be used. Indicator section 24 may be any appropriate indicating mechanism, whether mechanical or electronic, for indicating the pressure within pressurization section 22.

Pressurization section 22 contains a third aperture 44 for air flow communication with a needle connector 46. Needle connector 46 has a luer lock locking device 48 for an air tight connection with needle hub 1. Needle connector 48 is open at both ends for air flow communication between pressurization section 22 of pressure chamber 18 and epidural needle 1a attached to needle hub 1.

FIG. 2 illustrates the plunger 14, having longitudinal bore 16, in its original position. The one-way valve 28 of pressurization section 22 is closed. On the outer surface of the indicator section 24, indicia correlating the elastic force of the spring 36, of zero (0) mmHg, one hundred (100) mmHg, two hundred (200) mmHg, may be placed.

Figure 3A:
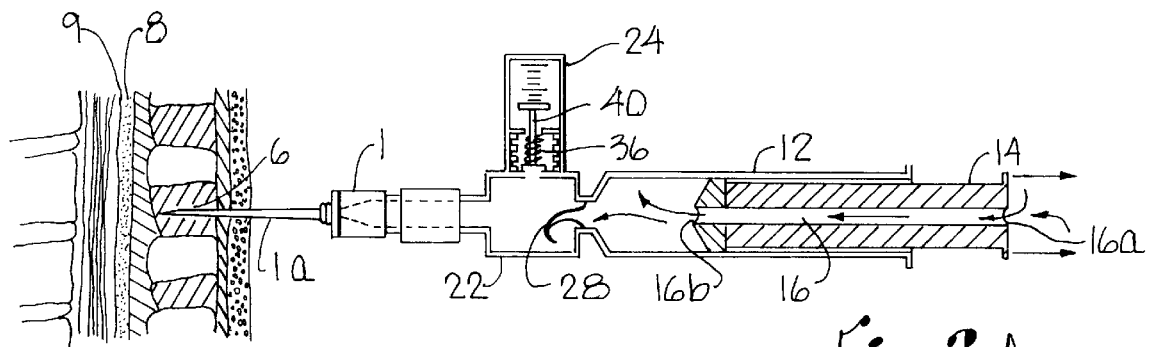
FIG. 3A is a cross-sectional view of the present invention illustrating its initial operating position after the needle has been inserted into the interspinous ligament with the plunger being pulled outwardly and air being drawn into the syringe from the longitudinal bore in the center of the plunger.
Figure 3B:
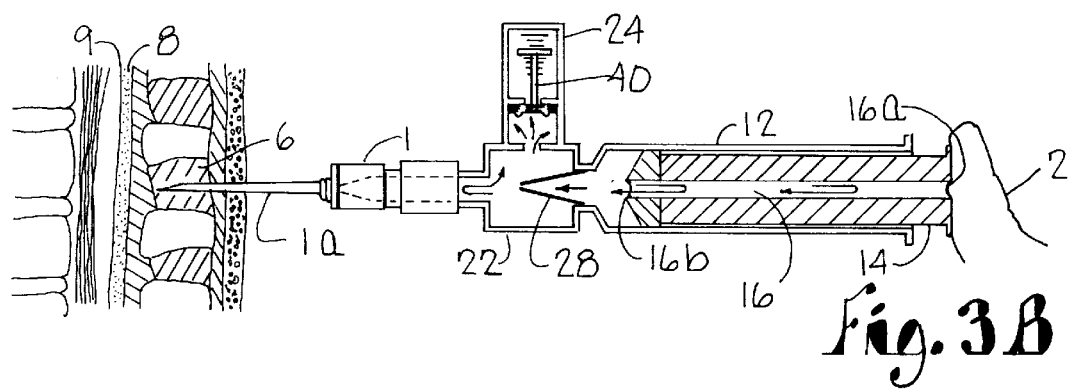
FIG. 3B is a cross-sectional view of the present invention illustrating pressurization while the needle is lodged in the interspinous ligament showing the plunger pushed inwardly with the operator's thumb covering the opening at the exposed end of the longitudinal bore of the plunger. The air in the syringe is being forced into the chamber through the one-way valve, and the pressure in the chamber is being built-up and indicated by the elevation of the pointer.
Figure 3C:
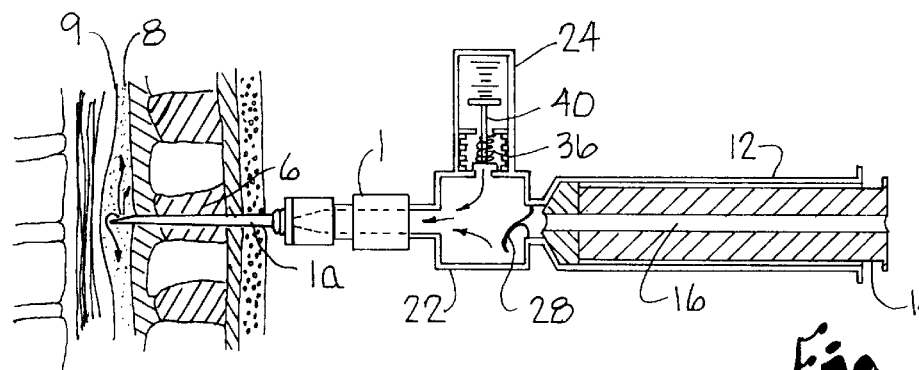
FIG. 3C is a cross-sectional view of the present invention after the needle has just entered the epidural space illustrating the dural deflection by positively pressurized air from the syringe and successful location of the epidural space.

Referring to FIGS. 3A, 3B and 3C, in operation, needle hub 1 having needle 1a is attached to the inventive syringe 10. Needle 1a is inserted into the interspinous ligament 6 towards the epidural space 8. The syringe 10 is positively pressurized while needle 1a is lodged in the interspinous ligament 6 with air. Pressurization section 22 of pressure chamber 18 is positively pressurized to a level optimal for deflection of the dura 9. Once pressurized, epidural needle 1a with the syringe 10 is pushed by two coordinated hands toward the epidural space 8 until indicator bar 40 drops sufficiently to reflect loss of positive pressure upon entrance of needle 1a into the epidural space 8. Syringe 10 may then be disengaged from needle hub 1 and the appropriate anesthetic or analgesic administering device may be engaged to needle hub 1 in order to administer the medication to the epidural space 8.

Specifically, FIGS. 3a, 3b, and 3c illustrate the syringe 10 in its operable positions. In FIG. 3a the user of the syringe 10 has inserted the epidural needle 1a into the interspinous ligament 6. The syringe 10 is shown in its initial position in FIG. 3a. At this point, the plunger 14 is pulled outwardly. The resulting negative pressure in the syringe housing 12 forces air into the exposed end 16a of longitudinal bore 16. One-way valve 28, however, prevents air from the pressure chamber, thereby allowing air to collect in the syringe housing 12.

FIG. 3b illustrates positive pressurization of the syringe 10. Pressurization is accomplished by placing the user's thumb 2 over the exposed end of the longitudinal bore 16. Any other suitable means like a plug such as an additional one-way valve may be employed to cover the exposed end of the longitudinal bore 16 once air has been introduced into syringe housing 12 via the exposed end 16a of longitudinal bore 16 of plunger 14. After the exposed end 16a of the longitudinal bore 16 has been plugged by the user's thumb 2 or other suitable means, the plunger 14 is depressed or pushed inwardly into the syringe housing 12 and the pressure within the syringe housing 12 becomes positive. The positive pressure forces open the one-way valve 28 and the air is forced through the one-way valve 28 into the pressurization section 22 of the pressure chamber 18. Because the needle 1a is lodged in the interspinous ligament 6, the air cannot escape through the tip of the needle 1a. Instead, the positive pressure from air compression builds up in the needle 1a and subsequently builds up in the pressurization section 22 and into the proximal portion 43 of the indicator section 24. The one-way valve 28 being closed prevents air from returning back into the syringe housing 12 causing the air to compress bellows 32 against the elastic force of the spring 36 leading to the elevation of indicator bar 40. The plunger 14 may be pulled outwardly again to restock the longitudinal bore 16 with air and plunger 14 may be pushed inwardly again with the air after appropriately plugging the exposed end 16a of longitudinal bore 16 to repeat the pressurization cycle, thus allowing the user to appropriately pressurize the pressure chamber 18. It is noteworthy that one cubic centimeter of completely compressed air yields approximately one hundred (100) mmHg pressure. The pressurization cycle may be repeated to determine whether needle 1a has entered the epidural space 8 rather than soft tissue. If the pressurized air is lost in the soft tissue it will form an air pocket around the tip of the needle 1a. Repeated pressurization cycles will rebuild positive pressure in chamber 18. If the pressurized air is lost in the epidural space 8 repeated pressurization cycles will not rebuild positive pressure in chamber 18 because of enormous volume of the epidural space 8.

FIG. 3c illustrates the syringe 10 after the needle 1a has been pushed through the interspinous ligament 6, successfully located the epidural space 8. This is accomplished when the user advances the needle 1a through the interspinous ligament 6 by pushing the needle 1a together with the syringe 10. Once the tip of the needle 1a has advanced through the interspinous ligament 6 and entered the epidural space 8, the lack of pressure on the tip of needle 1a creates a pressure gradient between the pressurization section 22 and the epidural space 8 through the needle 1a causing the air compressed in the pressurization section 22 to rush into the epidural space 8. This in turn causes deflection of the dura 9 as the air exiting the tip of the needle 1a deflects the dura 9 away from the tip of the needle 1a. The deflection of the dura 9 will protect the dura 9 from being punctured by the needle 1a, thus increasing the safety of the procedure. Visually, the user is quickly able to recognize that the needle 1a entered the epidural space 8 because the elastic force in the spring 36 pulls the indicator bar 40 back to its initial position due to the decreased pressure in the pressurization section 22. The movement of the indicator objectively identifies the loss of positive pressure which signals entrance of needle 1a into the epidural space 8.

While certain preferred embodiments of the present invention have been disclosed in detail, it is to be understood that various modifications in its structure may be adopted without departing from the spirit of the invention or the scope of the following claims.

We claim:

1. A pressurizable syringe comprising:

a syringe housing open at first and second ends;

a plunger having a longitudinal bore contained within said plunger, the longitudinal bore open at both ends, said plunger slidably connected inside said syringe housing from the first end of said syringe housing; and a hollow pressure chamber extending from the second end of said syringe housing having a one-way valve, a pressure indicator and a needle connector, the one-way valve air-tightly covering the opening of the second end of said syringe housing for allowing air from said syringe housing into said pressure chamber while preventing air contained within said pressure chamber from returning to said syringe housing, the pressure indicator attached to said pressure chamber for indicating the positive pressure within said pressure chamber, the needle connector extending from said pressure chamber for air-tightly receiving a needle.

2. A pressurizable syringe as recited in claim 1 wherein said pressure indicator is in air flow connection with said pressure chamber.

3. A pressurizable syringe as recited in claim 2 wherein said pressure indicator further comprises:

a transparent cylindrical case divided by a septum into a proximal portion and a distal portion, said proximal portion being the continuation of said pressure chamber;

a bellows having an open end and a closed end, the open end of said bellows air-tightly secured against the septum of said case;

a counterbalance spring having a first end and a second end, said spring biased to keep the closed end of said bellows against said pressure chamber, said spring placed within said bellows spanning the length of said bellows, the first end of said spring attached to the septum, the second end of said spring attached to the closed end of said bellows for counterbalancing said bellows upon compression; and a T-shaped bar pointer standing vertically within said spring and extends into the distal portion of said case for illustrating the presence of the positive pressure by its elevation which correlates with the elastic force of said spring from about 0–200 mmHg.

4. A pressurizable syringe as recited in claim 3 wherein said bellows rises upon coming in contact with positive pressure within said pressure chamber and lowers when coming in contact with negative pressure within said pressure chamber.

5. A pressurizable syringe as recited in claim 3 wherein said bellows rises upon coming in contact with positive pressure within said pressure chamber and lowers when coming in contact with zero pressure within said pressure chamber.

6. A pressurizable syringe as recited in claim 1 further comprising a locking mechanism for air-tightly locking a needle to said needle connector.

7. A pressurizable syringe as recited in claim 1 wherein said pressurizable syringe is molded plastic.

8. A method for objectively ascertaining the entry of a needle into the epidural space of a patient, comprising the steps of:

providing a pressurizable syringe comprising:

a syringe housing open at first and second ends;

a plunger having a longitudinal bore contained within said plunger, the longitudinal bore open at both ends, said plunger slidably connected inside said syringe housing from the first end of said syringe housing;

a hollow pressure chamber extending from the second end of said syringe housing having a one-way valve, a pressure indicator and a needle connector, the one-way valve air-tightly covering the opening of the second end of said syringe housing for allowing air from said syringe housing into said pressure chamber while preventing air contained within said pressure chamber from returning to said syringe housing, the pressure indicator attached to said pressure chamber for indicating the positive pressure with-in said pressure chamber, the needle connector extending from said pressure chamber for air-tightly receiving a needle;

attaching an epidural needle to said syringe;

inserting the needle into the patient's interspinous ligament and the ligamentum flavum towards the patient's epidural space;

pressurizing the pressure chamber of said syringe with air; and continuing to insert the needle towards the patient's epidural space until the pressure indicator indicates a drop in pressure, thereby objectively indicating entrance into the epidural space.

9. A method as recited in claim 8 wherein the step of pressurizing the pressure chamber further comprises pressurizing to approximately 200 mmHg.

10. A method for deflecting a patient's dura for preventing dural puncture, comprising the steps of:

providing a pressurizable syringe comprising:

a syringe housing open at first and second ends;

a plunger having a longitudinal bore contained within said plunger, the longitudinal bore open at both ends, said plunger slidably connected inside said syringe housing from the first end of said syringe housing;

a hollow pressure chamber extending from the second end of said syringe housing having a one-way valve, a pressure indicator and a needle connector, the one-way valve air-tightly covering the opening of the second end of said syringe housing for allowing air from said syringe housing into said pressure chamber while preventing air contained within said pressure chamber from returning to said syringe housing, the pressure indicator attached to said pressure chamber for indicating the positive pressure with-in said pressure chamber, the needle connector extending from said pressure chamber for air-tightly receiving a needle;

attaching an epidural needle to said syringe;

inserting the needle into the patient's interspinous ligament and the ligamentum flavum towards the patient's epidural space;

pressurizing the pressure chamber of said syringe with air; and continuing to insert the needle towards the patient's epidural space until the pressure indicator indicates a drop in pressure, thereby deflecting a patient's dura for preventing dural puncture.

11. A method as recited in claim 10 wherein the step of pressurizing the pressure chamber further comprises pressurizing to approximately 200 mmHg.

* * * * *